United States Patent [19]
Doten et al.

[11] Patent Number: 5,865,749
[45] Date of Patent: Feb. 2, 1999

[54] BLOOD FLOW METER APPARATUS AND METHOD OF USE

[75] Inventors: Gregory P. Doten, Crystal; Brian P. Brockway, Arden Hills, both of Minn.

[73] Assignee: Data Sciences International, Inc., St. Paul, Minn.

[21] Appl. No.: 744,360

[22] Filed: Nov. 7, 1996

[51] Int. Cl.$^6$ .................................................. A61B 8/00
[52] U.S. Cl. ............................................................ 600/443
[58] Field of Search .................................. 600/444, 443, 600/454, 465

[56] References Cited

U.S. PATENT DOCUMENTS

| | | |
|---|---|---|
| 4,198,987 | 4/1980 | Cain . |
| 4,227,407 | 10/1980 | Drost ........................................ 73/194 |
| 4,622,978 | 11/1986 | Matuso et al. ........................... 128/663 |
| 4,787,395 | 11/1988 | Yanashima et al. ...................... 600/454 |
| 4,809,703 | 3/1989 | Ishikawa et al. ......................... 600/454 |
| 4,866,613 | 9/1989 | Amemiya et al. ........................ 600/454 |
| 4,905,206 | 2/1990 | Nishiyama et al. ........................ 367/90 |
| 5,046,500 | 9/1991 | Fehr ..................................... 128/661.09 |
| 5,103,825 | 4/1992 | Hokanson . |
| 5,107,466 | 4/1992 | Nishiyama et al. ........................ 367/90 |
| 5,111,825 | 5/1992 | Nishiyama et al. ................. 128/661.09 |
| 5,113,867 | 5/1992 | Janszen . |
| 5,156,152 | 10/1992 | Yamazaki et al. ....................... 600/454 |
| 5,188,106 | 2/1993 | Nappholz et al. ....................... 128/419 |
| 5,291,892 | 3/1994 | O'Donnell ............................... 600/454 |
| 5,383,462 | 1/1995 | Hall ........................................ 600/454 |
| 5,476,097 | 12/1995 | Robinson ........................... 128/660.05 |
| 5,544,656 | 8/1996 | Pitsillides et al. .................. 128/661.04 |

FOREIGN PATENT DOCUMENTS

| | | |
|---|---|---|
| 1215659 | 2/1986 | U.S.S.R. . |
| 1734697A | 5/1992 | U.S.S.R. . |

OTHER PUBLICATIONS

"A Signal Processing Approach", *Estimation of Blood Velocities Using Ultrasound*, Cambrige University Press, Great Britain, 4 pages, (1996).

Jean–Yves David, et al., "Modern Spectral Analysis Techniques for Blood Flow Velocity and Spectral Measurements with Pulsed Doppler Ultrasound", *IEEE*, vol. 38, No. 6, pp. 589–596, (Jun. 1991).

Chihiro Kasai, et al., "Real–Time Two–Dimensional Blood Flow Imaging Using an Autocorrelation Technique", *IEEE*, vol. SU–32, No. 3, pp. 458–464, (May 1985).

K. F. Pitsillides, et al., "Biotelemetry of Cardiovascular Hemodynamic Measurements in Miniswine", *IEEE*, vol. 39, No. 9, pp. 982–986, (Sep. 1992).

Mark C. Shults, et al., "A Telemetry–Instrumentation System for Monitoring Multiple Subcutaneously Implanted Glucose Sensors", *IEEE*, vol. 41, No. 10, pp. 937–942, (Oct. 1994).

(List continued on next page.)

*Primary Examiner*—Marvin M. Lateef
*Assistant Examiner*—Maulin Patel
*Attorney, Agent, or Firm*—Schwegman, Lundberg, Woessner, and Kluth, P.A.

[57] ABSTRACT

A strobed blood flow meter provides periodic measurements of blood flow velocity or volumetric blood flow over a cardiac cycle at reduced average power consumption, which is advantageous for reducing battery size, and extending device battery life, such as in an implantable application. Continuous wave Doppler, pulsed Doppler, laser Doppler, transit time, electromagnetic flow, and thermal dilution techniques are included. Strobing provides higher level excitation during active periods, which improves signal-to-noise ratio, and provides a low power standby mode during an idle time between active periods. The invention may be used for chronic or acute applications. Doppler or other signals may be telemetered from an implanted portion of the flow meter for further signal processing to extract velocity or volumetric flow. Alternatively, such signal processing is also implanted, such that the velocity signal can be telemetered to an remote monitor.

20 Claims, 15 Drawing Sheets

OTHER PUBLICATIONS

Yoshiharu Yonezawa, et al., "A Miniaturized Ultrasonic Flowmeter and Telemetry Transmitter For Chronic Animal Blood Flow Measurements", *Eng. Symp. ISA Biomed. Sci. Instrument*, pp. 107–111, (1989).

Y. Yonezawa, et al., "Radio Telemetry Directional Ultrasonic Blood Flowmeter for Use with Unrestrained Animals", *Med. & Biol. Eng. & Comput.*, pp. 659–665, (Nov. 1992).

"Copy of International Search Report", for PCT/US 97/20038, by Examiner D. Lemercier, 2, (May 19, 1998).

5,865,749

BLOOD FLOW METER APPARATUS AND METHOD OF USE

FIELD OF THE INVENTION

This invention relates to estimation of fluid flow, and more particularly to a chronic or acute measurement of blood flow in a blood vessel.

BACKGROUND

There are many applications in clinical and research medicine in which measurement or estimation of volumetric blood flow within a blood vessel is desirable. One method of making such measurements uses ultrasonic Doppler techniques to measure blood flow velocity and thereby estimate volumetric blood flow. Velocity of an object is often measured using the Doppler effect. Single frequency ultrasonic energy is transmitted into an area of tissue containing the blood flow to be measured. This insonification of the area is typically referred to as illumination. Resulting ultrasonic energy is reflected, or backscattered, from the illuminated area. Energy reflected from moving targets, such as fluid and blood cells, will be shifted in frequency from the illuminating frequency according to the well-known Doppler effect. The Doppler shifted frequency provides a measure of the blood flow velocity.

In clinical and research applications, it is often necessary to study blood flow for an extended period of time. Thus, in ambulatory living organisms, such as animal or human subjects, there is a need in the art to provide a battery-powered ultrasonic Doppler blood flow meter for measuring blood flow velocity for an extended period of time, allowing a human or animal patient freedom of movement during the study and minimizing the need for supervision by the clinician. There is also a need in the art to provide a small, low-power ultrasonic Doppler blood flow meter that is suitable for implantation in a human or animal subject. There is a further need in the art to provide an implantable ultrasonic Doppler blood flow meter that maintains adequate signal-to-noise (SNR) ratio for accurate velocity estimation.

SUMMARY

The present invention includes a method and apparatus for estimating blood flow or blood flow velocity in a blood vessel over a period of time. According to the method, at least part of the measurement circuits used to estimate blood flow are automatically activated only during the time an estimate is being obtained. At least part of the measurement circuits are automatically deactivated during the time an estimate is not being obtained. These steps are performed repeatedly to provide a sequence of blood flow estimates forming a blood flow waveform indicative of blood flow. More than one estimate is typically required to obtain a waveform representative of the blood flow.

The steps of activating and deactivating at least part of the measurement circuits is repeatedly performed sufficiently frequently, either periodically or at irregular intervals, such that the blood flow waveform substantially represents the variable blood flow. Power to at least a portion of the measurement circuits is reduced or interrupted while the measurement circuits are deactivated.

Measurement of blood flow can be obtained through various blood flow measurement techniques, including: continuous wave (CW) Doppler flow measurement, pulsed Doppler flow measurement, laser Doppler flow measurement, transit time flow measurement, thermal dilution flow measurement, electromagnetic flow measurement, or other suitable flow measurement technique.

In several embodiments, a basebanded Doppler-shifted signal provides the blood flow estimate. In other embodiments, a blood flow output signal is derived from the basebanded Doppler-shifted signal and provided as the blood flow estimate.

Thus, the present invention provides a strobed blood flow meter, such as an implantable strobed ultrasonic Doppler blood flow meter, having reduced average power consumption, which is advantageous for reducing battery size, extending battery life, and improving signal-to-noise ratio.

BRIEF DESCRIPTION OF THE DRAWINGS

In the drawings, like numerals describe substantially similar components throughout the several views.

DETAILED DESCRIPTION

Figure 1:
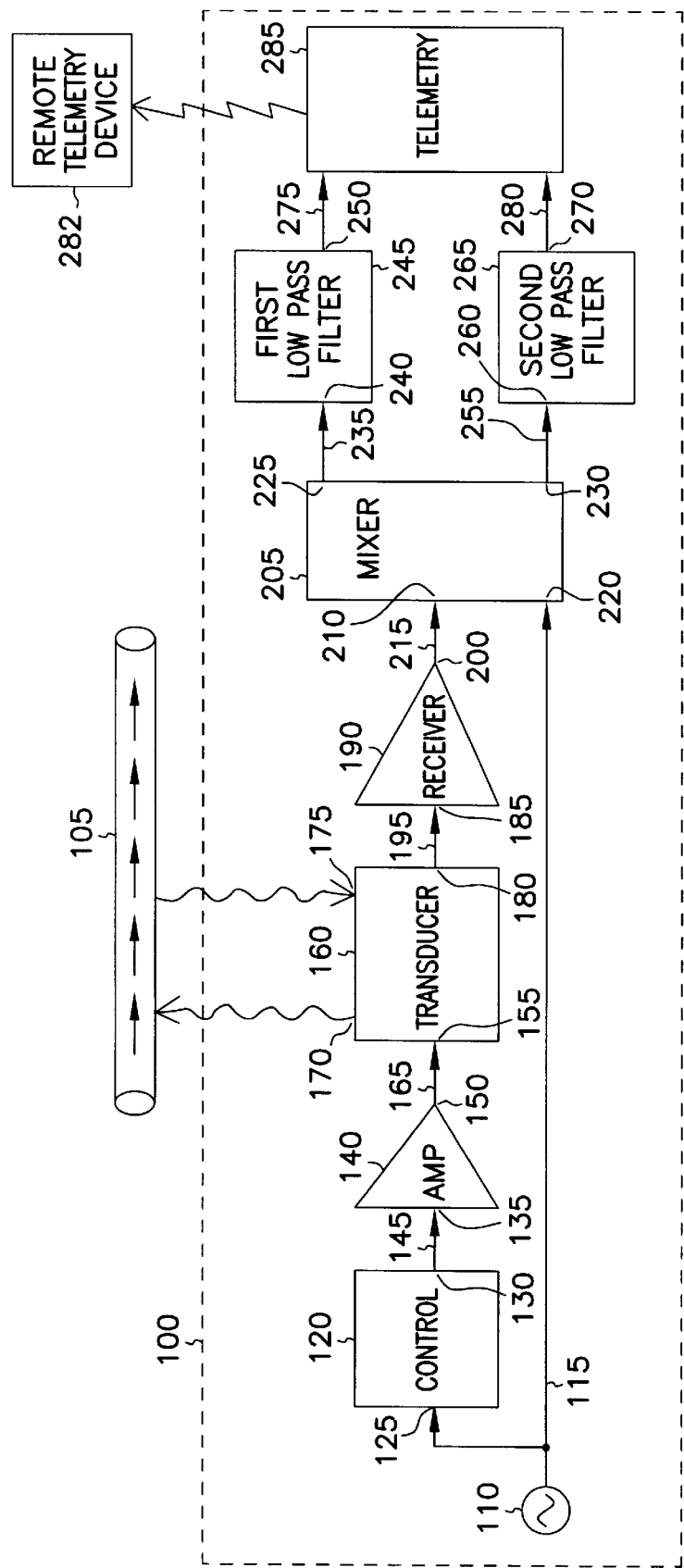
FIG. 1 is a block diagram of one embodiment of the invention.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present invention provides a strobed blood flow meter useful for chronic or acute estimates of blood flow or blood flow velocity and having reduced average power consumption, which has advantages that include reducing battery size and extending battery life. As discussed and defined herein, estimating volumetric blood flow and blood flow velocity are understood as interchangeable concepts, since estimates of volumetric blood flow are obtained from estimates of blood flow velocity by multiplying blood flow velocity with a known constant cross-sectional area of a blood vessel. When the cross-sectional area of the blood vessel is unknown, a signal proportional to estimates of blood flow can still be provided from estimates of blood flow velocity since the cross-sectional area of the blood vessel is assumed to be relatively constant.

As used herein, the term "strobing" is defined as repeatedly estimating blood flow velocity during a period of interest, as discussed below. In a living organism having a circulatory system with a cardiac cycle, which is defined as the period between successive heartbeats, the period of interest for strobing may be one or more such cardiac cycles. However, it is also desirable to repeatedly estimate blood flow velocity over a period of interest when no cardiac cycle is present. For example, certain embodiments of an artificial heart pump may be implemented without the periodic pulsing associated with a heartbeat. In such systems, it may still be desirable to repeatedly estimate blood flow velocity over some other period of interest.

As will be described in detail below, the present invention encompasses strobing or automatically activating certain portions of the blood flow meter during an active period in order to obtain an ultrasonic Doppler blood flow velocity estimate, and later automatically deactivating these portions of the blood flow meter during an idle time between such estimates. As a result, average power consumption is advantageously reduced. Strobing according to the present invention includes a wide variety of blood flow measurement techniques, including, but not limited to: ultrasonic Doppler blood flow measurement, such as both continuous wave (CW) and pulsed Doppler blood flow measurements; transit time measurements; electromagnetic flow measurements; thermal dilution measurements; and laser Doppler measurements, each of which is described further below.

FIG. 1 is a block diagram illustrating one embodiment of the present invention. In FIG. 1, strobed ultrasonic blood flow meter 100 is capable of being implanted in a human or animal subject for measurement of blood flow in blood vessel 105. Blood flow meter 100 comprises oscillator 110, which is a sine or square wave oscillator operating at a carrier frequency in an ultrasonic region of the frequency spectrum, typically in the 5–20 MHz range, though other frequencies are also possible. The ultrasonic sine or square wave output signal of oscillator 110 at node 115 is referred to as a carrier signal. The carrier signal frequency at node 115 is in the ultrasonic frequency range, and is electrically coupled to a control circuit 120 at control circuit oscillator input 125. Control circuit 120 produces at control circuit output 130 a resulting electrical strobed ultrasonic-frequency signal (shown as signal 145V in FIG. 5A) which is electrically coupled to amplifier input 135 of power amplifier 140 through node 145. In response, amplifier 140 produces a resulting electrical strobed amplified ultrasonic-frequency signal at amplifier output 150, which is electrically coupled through node 165 to transducer electrical input 155 of transducer 160. In response, transducer 160 provides, at transducer ultrasound output 170, ultrasonic energy that is mechanically or acoustically coupled to tissue including blood vessel 105. In this patent application, providing ultrasonic energy, insonifying, and insonating, are all referred to generally as illuminating.

Illumination of blood vessel 105 results in a reflected Doppler-shifted ultrasound signal, also referred to as a backscattered signal, that is received at transducer ultrasound input 175, and converted by transducer 160 into a Doppler-shifted electrical signal at transducer electrical output 180. The Doppler-shifted electrical signal is electrically coupled through node 195 to receiver input 185 of receiver 190, which provides a buffered Doppler-shifted signal in response thereto at receiver output 200.

Mixer 205 receives the buffered Doppler-shifted signal at mixer input 210 through node 215. Mixer 205 also receives through node 115 the carrier signal of oscillator 110 at mixer oscillator input 220. Mixer 205 performs a demodulation function by quadrature mixing, as described below, producing an in-phase (I) signal at in-phase (I) output 225 and a phase-shifted (Q) signal, which is 90 degrees out of phase with respect to the I signal, at phase-shifted (Q) output 230. The I and Q signals each have components that include difference and sum frequency components that are approximately equal to the respective difference and sum of the frequencies of the carrier signal and the buffered Doppler-shifted signal. The I and Q signals may also contain a carrier frequency component, also referred to as carrier feedthrough.

The I signal is electrically coupled through node 235 to a first low pass filter input 240 of first low pass filter 245. First low pass filter 245 removes the carrier feedthrough and the sum frequency components of the I signal, and provides the difference frequency component at the first low pass filter output 250. The difference frequency component at the first low pass filter output 250 is referred to as the basebanded in-phase Doppler signal, or the basebanded I Doppler signal. Similarly, the Q signal is electrically coupled through node 255 to a second low pass filter input 260 of second low pass filter 265. Second low pass filter 265 removes the carrier feedthrough and the sum frequency components of the Q signal and provides the difference frequency component at the second low pass filter output 270. The difference frequency component at the second low pass filter output 250 is referred to as the basebanded phase-shifted Doppler signal, or the basebanded Q Doppler signal.

The basebanded I and Q Doppler signals are electrically coupled through respective nodes 275 and 280 to respective inputs of telemetry circuit 285. In one embodiment, the basebanded I and Q Doppler signals are remodulated with a telemetry carrier frequency for transmission to a remote telemetry device 282, such as an external telemetry receiver. In another embodiment, as described below, an analog velocity output signal is produced, which is encoded, such as by pulse position modulation, for transmission to remote telemetry device 282. Thus, telemetry circuit 285 allows transmission of the signals corresponding to the basebanded I and Q Doppler signals from implanted blood flow meter 100 to a remote telemetry device 282 for further processing.

In one embodiment, this further processing includes velocity determination according to the well-known Doppler equation, illustrated in Equation (1).

$$v = \frac{f_d C}{2 f_c \cos\theta} \quad (1)$$

In Equation (1): v is the blood flow velocity to be determined; $f_d$ is the (basebanded) received Doppler shifted frequency reflected from the blood flow; C is the speed of sound in the medium, e.g. tissue; $f_c$ is the carrier frequency; and θ is the angle formed by the velocity vector of the blood flow and the path along which the illuminating ultrasonic energy is provided.

Figure 2:
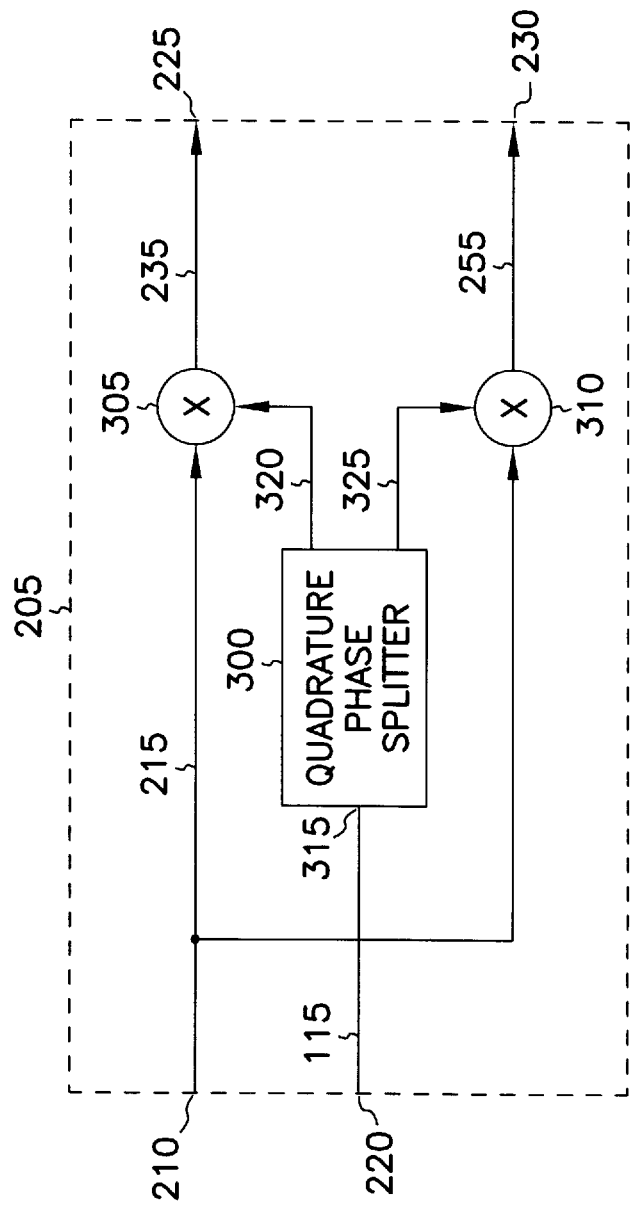
FIG. 2 is a block diagram illustrating one embodiment of the mixer of FIG. 1 in more detail.

FIG. 2 is a block diagram illustrating one embodiment of mixer 205 in more detail. In FIG. 2, mixer 205 includes quadrature phase splitter 300, first multiplier 305, and second multiplier 310. Splitter 300 receives, through node 115, the carrier signal at splitter input 315, and produces in response thereto a resulting in-phase carrier signal at node 320 and a phase-shifted carrier signal at node 325 that is phase-shifted by 90 degrees with respect to the in-phase carrier signal. The in-phase carrier signal at node 320 and the phase-shifted carrier signal at node 325 are substantially quadrature balanced, i.e. they are substantially matched in amplitude, and have a phase difference which is very close to 90 degrees. The buffered Doppler signal at node 215 is multiplied at first multiplier 305 by the in-phase carrier signal at node 320 to produce the I signal at node 235. The buffered Doppler signal at node 215 is also multiplied at second multiplier 310 by the phase-shifted carrier signal at node 325 to produce the Q signal at node 255.

Figure 3:
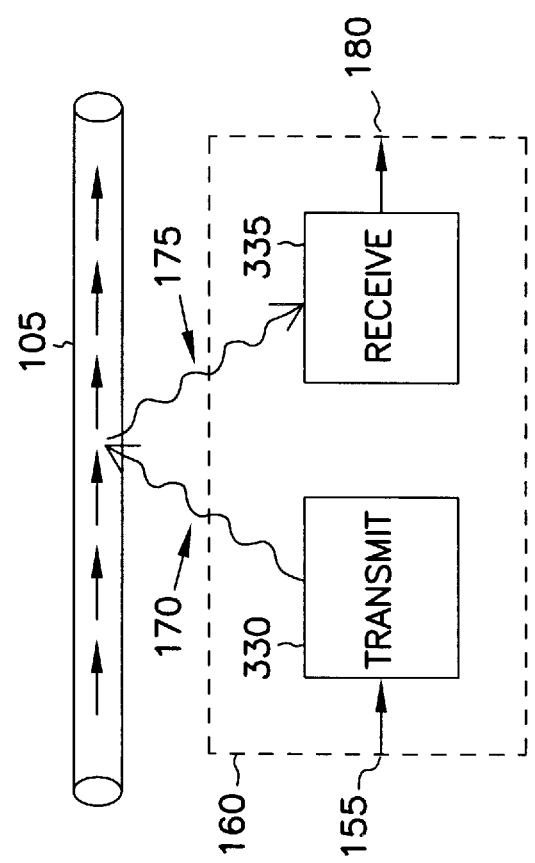
FIG. 3 is a block diagram illustrating one embodiment of the transducer of FIG. 1 in more detail.

FIG. 3 is a block diagram illustrating one embodiment of transducer 160 in more detail, in relation to blood vessel 105. In FIG. 3, transducer 160 includes ultrasound transmit transducer 330 and ultrasound receive transducer 335. Transmit and receiver transducers 330 and 335 are preferably single piston piezoelectric transducers, comprised of materials such as lead zirconate titanate (PZT) crystal or composite materials. Other piezoelectric crystal, ceramic, or polymer, or any other suitable transducer may also be used.

Transmit transducer 330 receives the electrical strobed amplified ultrasonic-frequency signal at input 155 and provides, or launches, continuous wave (CW) ultrasonic energy at transducer ultrasound output 170 for illumination of blood vessel 105. Illumination of blood vessel 105 results in a reflected Doppler-shifted ultrasound signal at transducer ultrasound input 175 that is received by receive transducer 335 and converted into an electrical received Doppler-shifted signal at transducer electrical output 180. In FIG. 3, separate transmit and receive transducers 330 and 335 are used for simultaneously illuminating and receiving CW Doppler ultrasound. However, it is understood that a single transducer could also be used for sequentially illuminating and receiving pulsed Doppler ultrasound, as described below.

Figure 4:
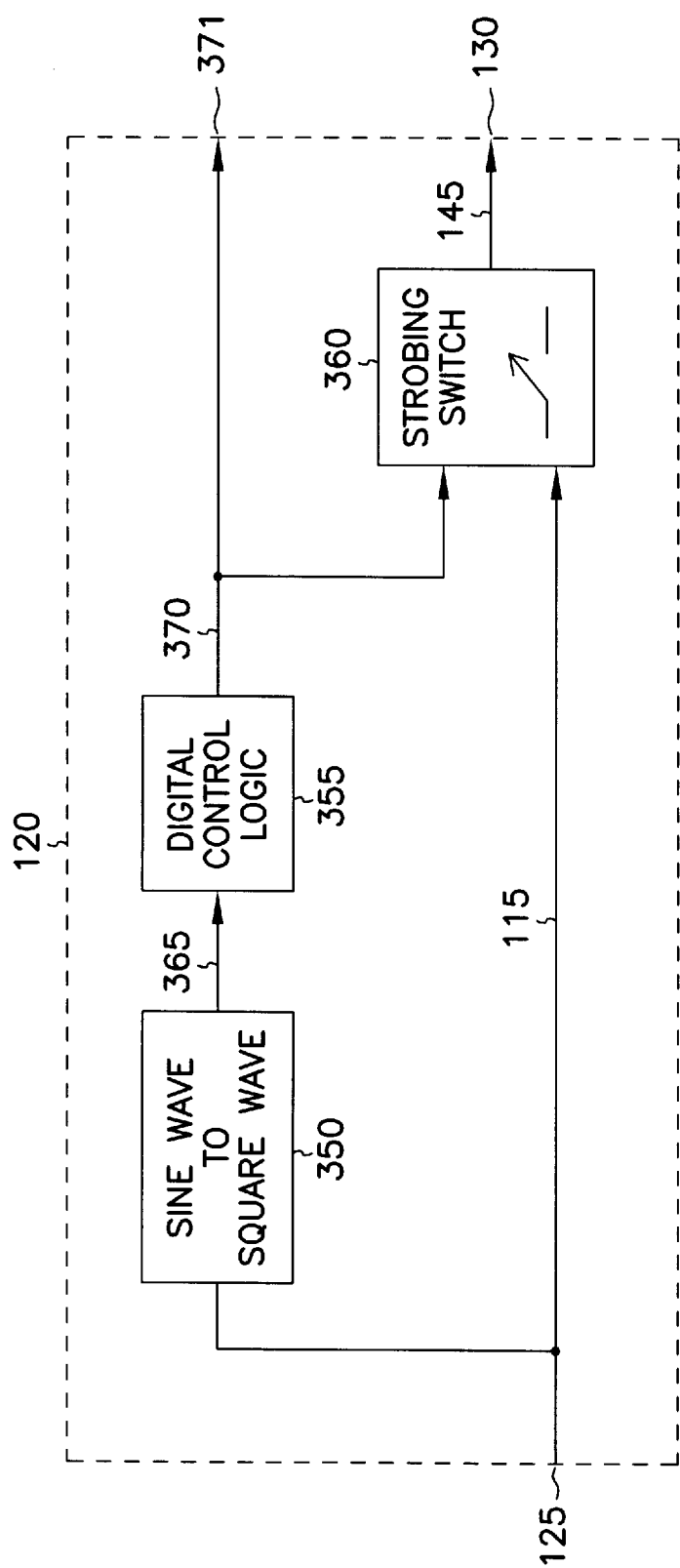
FIG. 4 is a block diagram illustrating one embodiment of the control circuit of FIG. 1 in more detail.

FIG. 4 is a block diagram illustrating one embodiment of control circuit 120 in more detail. In FIG. 4, control circuit 120 includes sine wave to square wave converter 350, digital control logic 355, and strobing switch 360. Converter 350 receives the carrier signal at node 115 and provides to digital control logic 355 a square wave clock signal at node 365, which can be divided down to lower frequencies if desired. Converter 350 is omitted if oscillator 110 is a square wave, rather than a sine wave oscillator. Logic 355 provides a periodic strobing control signal at node 370, also available at strobing control signal output 371, to control the conductance of the carrier signal at node 115 through strobing switch 360 to control circuit output 130. However, the periodic strobing control signal at node 370 could alternatively be provided at irregular intervals. A resulting electrical strobed ultrasonic-frequency signal is provided through node 145 for amplification by amplifier 140 and conversion into ultrasound energy by transducer 160.

Figure 5A:
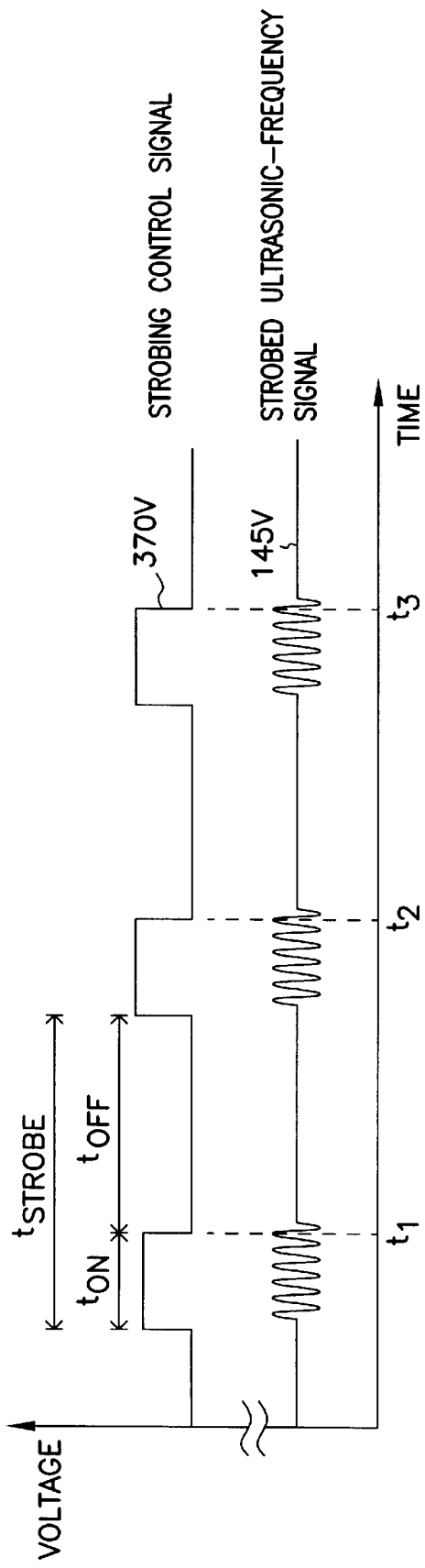
FIG. 5A is a graph illustrating generally voltage vs. time waveforms for one embodiment in which the invention is operated.
Figure 5B:
FIG. 5B is a graph illustrating generally a velocity vs. time signal in operation of the embodiment of FIG. 5A, but on a compressed time scale with respect to the illustration of FIG. 5A.

FIG. 5A is a voltage vs. time graph illustrating generally timing in one embodiment in which the present invention is operated. FIG. 5A includes strobing control signal 370V at node 370 and the strobed ultrasonic frequency signal 145V at node 145. A corresponding velocity vs. time graph is illustrated in FIG. 5B, but with time illustrated on a compressed time scale with respect to that in FIG. 5A. In FIG. 5A, strobing control signal 370 is a periodic control signal having a corresponding strobing period, $t_{strobe}$. The strobing period is comprised of an active period, $t_{on}$, and an idle period, $t_{off}$.

During the active period of the strobing control signal 370V, the carrier frequency signal at node 115 is conducted to node 145 through the strobing switch 360, as illustrated during the corresponding portion of the strobed ultrasonic frequency signal 145V. During the idle period of the strobing control signal 370V, the carrier frequency signal at node 115 is isolated from node 145 by the strobing switch 360, as illustrated during the corresponding portion of the strobed ultrasonic frequency signal 145V. Blood vessel 105 is illuminated during each active period of the strobing control signal 370V, as illustrated in FIG. 5A. Velocity is determined near the end of each active period of the strobing control signal 370V, such as at times $t_1$, $t_2$, and $t_3$, as illustrated in FIGS. 5A and 5B.

Blood velocity will vary depending on the size and physiological location of the blood vessel 105 being measured. Blood velocity will also vary as a function of time during the cardiac cycle, i.e. during and between successive heartbeats. One embodiment of the present invention uses a programmably adjustable strobing frequency, which is the inverse of the strobing period. The strobing frequency should be high enough to provide a representative estimated velocity vs. time waveform both during the cardiac cycle and over many cardiac cycles. For example, in most larger mammals, heart rate varies from between 40 to 200 beats per minute. A strobing frequency of 50 Hz respectively provides 75 and 15 estimated velocity data points for each of these respective heart rates. For smaller mammals, such as rats, heart rate may approach 400 beats per minute. Increasing strobing frequency to 100 Hz would still allow 15 estimated velocity data points for this case.

The particular strobing frequency may be selected to obtain the desired time resolution of velocity estimates. The desired time resolution of velocity estimates may in turn be selected to accommodate the expected rate of change of blood flow velocity in the blood vessel. The rate of change of the blood flow velocity is typically higher for an arterial blood vessel 105 that is more proximal to the heart than for an arterial blood vessel 105 that is more distal from the heart or for a venal blood vessel 105. As set forth above, $t_{strobe}$ will exceed $t_{on}$. But the maximum value of $t_{strobe}$ will depend on many factors, including whether an accurate reconstruction of the velocity waveform is needed or whether the velocity estimates are used only to determine blood flow, such that fewer estimates per cardiac cycle may suffice.

In one embodiment, active period, $t_{on}$, is minimized to minimize average power consumption or to obtain other advantages, as described below. However, the minimum active period is typically longer than some combination of:

a system bandwidth; a stabilization time; and a mean-frequency estimation time.

The system bandwidth is defined as the inverse of the maximum expected basebanded I and Q Doppler signal frequencies, which can be calculated from the well-known Doppler equation for a particular blood velocity.

The stabilization time is the time required to power up and stabilize certain electronic circuits which are powered down during the idle period. The required stabilization time may be dominated by, for example, the filter time-constants of first and second low pass filters 245 and 265, if these filters were powered down during the idle period. In another example, the required stabilization time may be dominated by the charging of a power supply output capacitor from which power is supplied to those electronic circuits that were turned off during the idle period. Separate control signals may be provided to individual electronic circuits to tailor the time that the circuits are powered to meet their individual stabilization requirements. For example, first and second low pass filters 245 and 265 may be turned on prior to providing the electrical signal to drive transducer 160 to accommodate longer stabilization time requirements of first and second low pass filters 245 and 265.

The mean frequency estimation time is determined by the number of samples of the basebanded I or Q Doppler signals at respective nodes 275 and 280 that must be acquired to accurately estimate the blood velocity for a particular velocity estimate. The mean frequency estimation time depends, in turn, on the particular mean frequency estimation technique used. In one embodiment, sophisticated digital signal processing techniques are used to extract a relatively accurate mean frequency estimate from as few as 8 of the samples. In another embodiment, zero-cross detection techniques are used to provide a root mean square (rms) reading of mean frequency from more than 100 samples.

The present invention uses strobed ultrasonic energy, which advantageously reduces its average power consumption. This is particularly important when power is drawn from a fixed resource, such as a battery, which is implanted in vivo together with the electronics of blood flow meter 100 and cannot be easily replaced. In such situations, the reduced average power consumption of the present invention is critical for extending battery life of blood flow meter 100. The average power consumption of the present invention is illustrated by Equation (2).

$$\text{Power} = \frac{P_{on}t_{on} + P_{off}t_{off}}{t_{strobe}} \quad (2)$$

In Equation (2), $P_{on}$ is the power consumption during the active period and $P_{off}$ is the power consumption during the idle period. As explained below, most of the electronics of blood flow meter 100 are powered on during the active period, but only a subset of these electronics are powered on during the idle period. For this reason, $P_{on}$ exceeds $P_{off}$. Thus, as illustrated in Equation (2), average power consumption is minimized by: reducing the duration of the active period; and, increasing the strobing period; and, decreasing both $P_{on}$ and $P_{off}$, particularly $P_{on}$.

Figure 6:
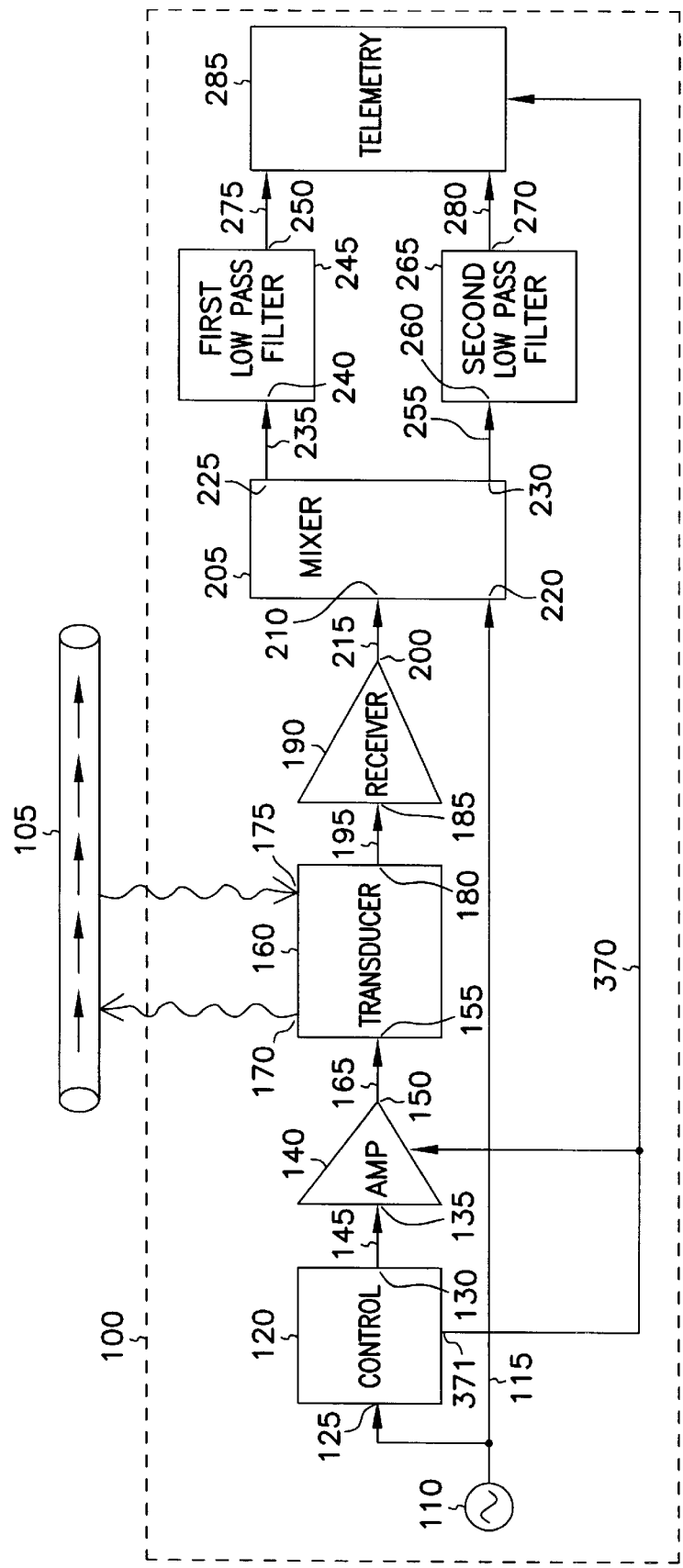
FIG. 6 is a block diagram illustrating one embodiment of the present invention in which certain components are turned off during the idle period.

FIG. 6 is a block diagram illustrating one embodiment of the present invention in which only amplifier 140 and telemetry 285 are turned off during the idle period. The strobing control signal at node 370 is electrically coupled to switchably control the conductances between each of amplifier 140 and telemetry 285 blocks and their respective power supplies. Transducer 160 typically does not draw any bias current, but use of any transducer that does draw bias current could similarly have its bias current switchably controlled by strobing control signal 370. By leaving other blocks powered during the idle period, stabilization time is reduced, as described above. However, this embodiment does not minimize average power consumption as much as other possible embodiments.

Figure 7:
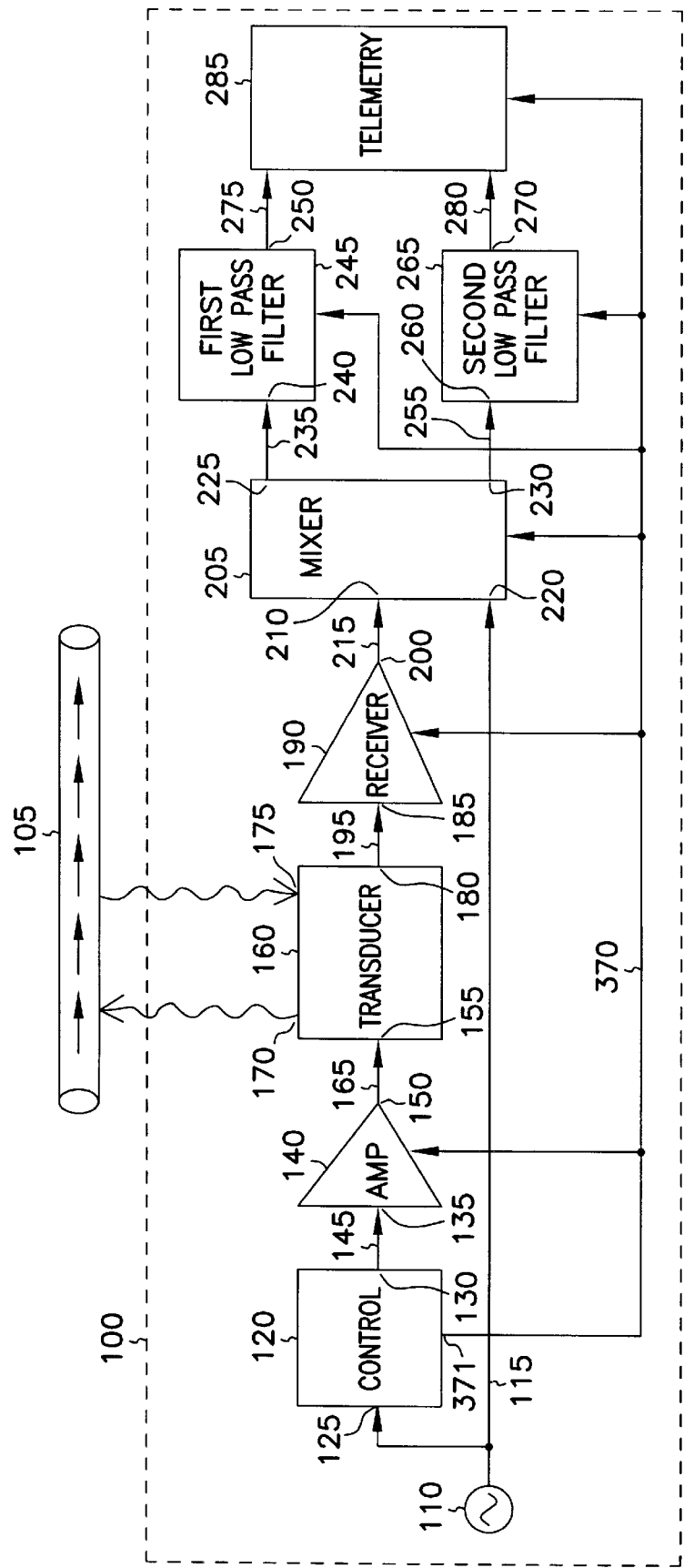
FIG. 7 is a block diagram illustrating another embodiment of the present invention in which certain components are turned off during the idle period.

FIG. 7 is a block diagram illustrating another embodiment of the present invention in which amplifier 140, receiver 190, mixer 205, first and second low pass filters 245 and 265, and telemetry 285 are all turned off during the idle period. The strobing control signal at node 370 is electrically coupled to switchably control, either independently or in groups, the conductances between each of amplifier 140, receiver 190, mixer 205, first and second low pass filters 245 and 265, and telemetry 285 and their respective power supplies. Since more components are powered down during the idle period, this embodiment decreases average power consumption further from that of FIG. 6, but stabilization time may be increased, as explained above.

Figure 8:
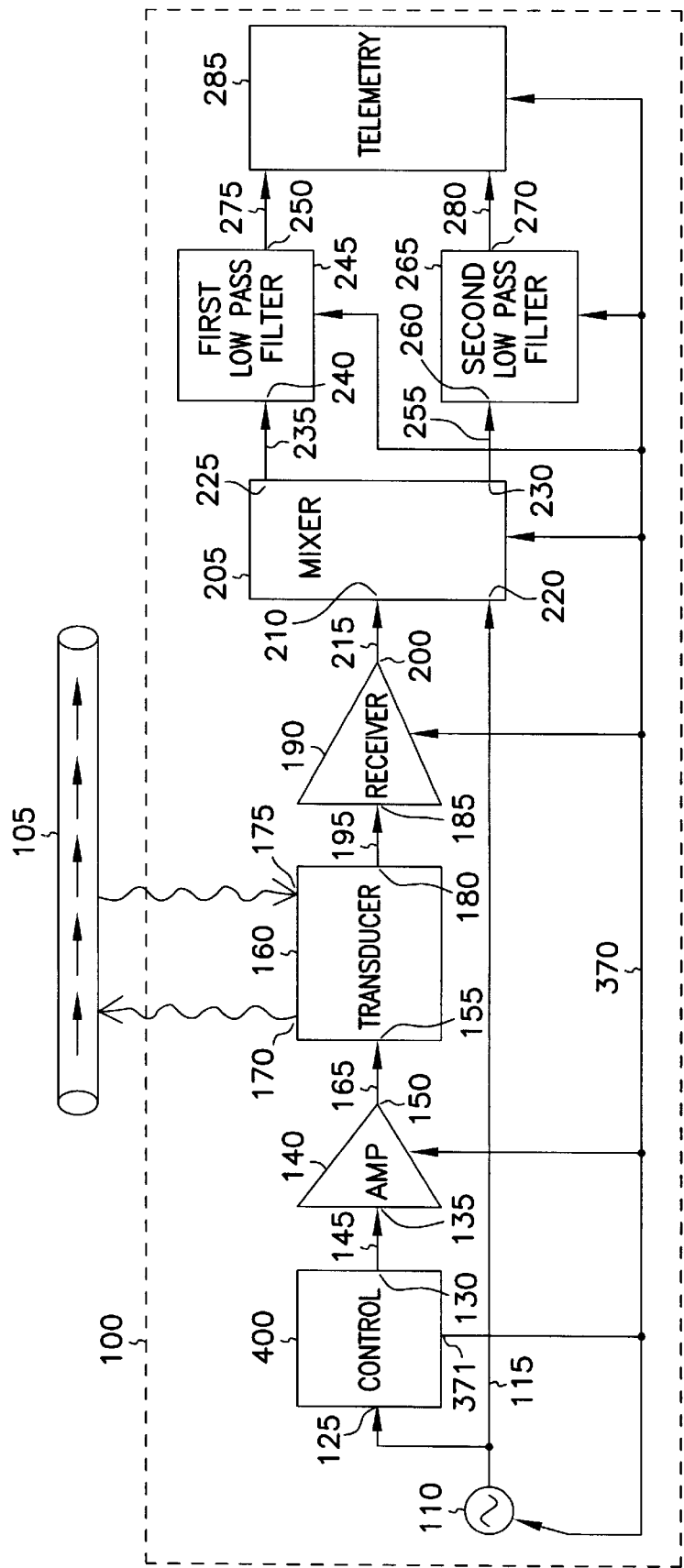
FIG. 8 is a block diagram illustrating a further embodiment of the present invention in which certain components are turned off during the idle period.

FIG. 8 is a block diagram illustrating another embodiment of the present invention in which oscillator 110, amplifier 140, receiver 190, mixer 205, first and second low pass filters 245 and 265, and telemetry 285 are all turned off during the idle period. The strobing control signal at node 370 is electrically coupled to switchably control, either independently or in groups, the conductances between each of oscillator 110, amplifier 140, receiver 190, mixer 205, first and second low pass filters 245 and 265, and telemetry 285 and their respective power supplies. FIG. 8 uses a control circuit 400, which is illustrated in more detail in FIG. 9. Since more components are powered down during the idle period, this embodiment decreases average power consumption further from that of FIGS. 6–7.

Figure 9:
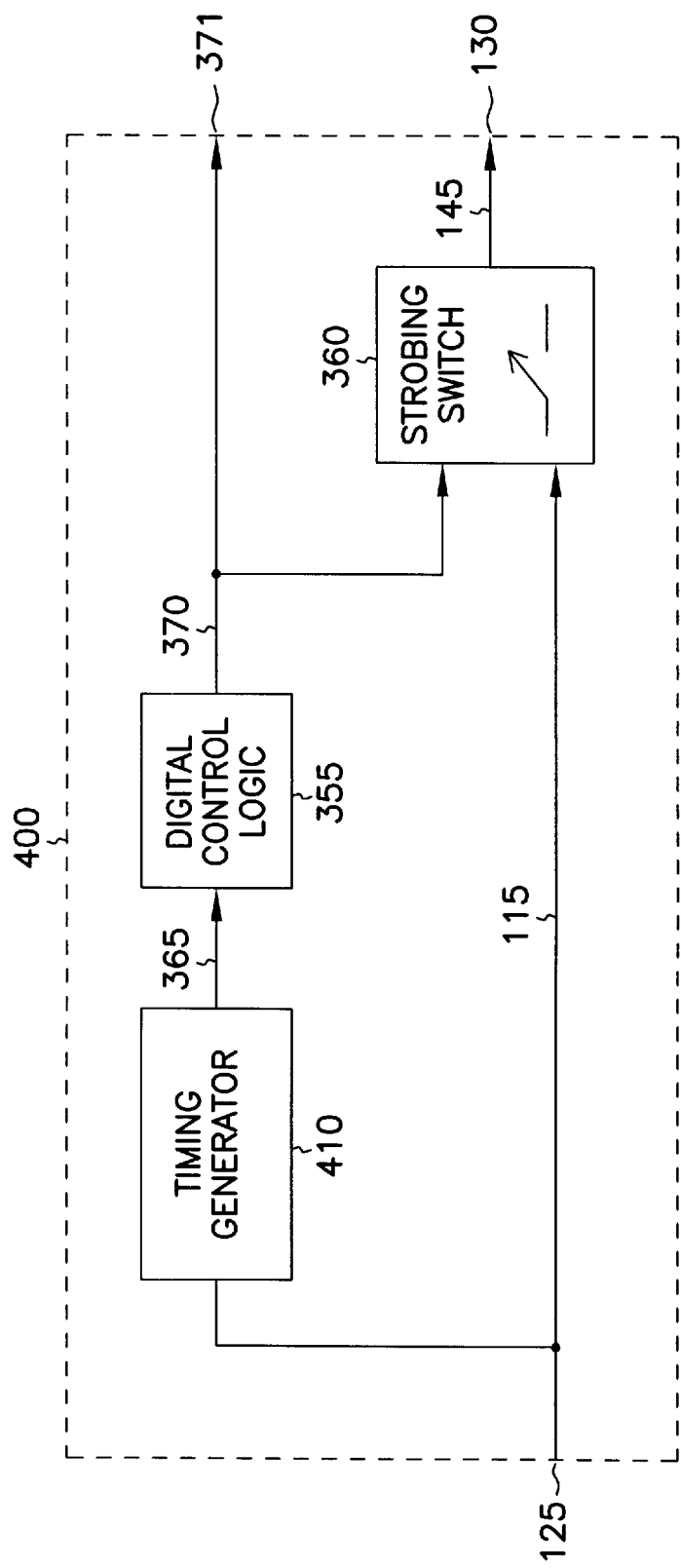
FIG. 9 is a block diagram illustrating in more detail the control circuit of FIG. 8 in more detail.

FIG. 9 is a block diagram illustrating in more detail the control circuit 400 of FIG. 8. In FIG. 9, a separate timing generator 410 is provided for coupling a clock signal through node 365 to digital control logic 355. As in the embodiments illustrated in FIGS. 1 and 6–7, at least a portion of the digital control logic remains powered during the idle period in the embodiment illustrated in FIGS. 8–9. In the embodiment illustrated in FIGS. 8–9, the timing generator 410 also remains powered during the idle period. Timing generator 410 is capable of being operated at a lower frequency than the ultrasonic frequencies of oscillator 110. Use of timing generator 410 allows the higher frequency oscillator 110 to be powered down during the idle period. This results in further average power savings in some implementations of the present invention.

Thus, the invention described above in FIGS. 1–9 provides a method of estimating the velocity of blood flow in a blood vessel. At least part of the measurement circuits are automatically activated only during the time an estimate is being obtained. At least part of the measurement circuits are deactivated during the time an estimate is not being obtained. These steps are performed repeatedly to provide a sequence of blood flow estimates forming a blood flow waveform indicative of blood flow. More than one estimate is required to obtain the blood flow waveform.

According to one embodiment of the present invention, ultrasonic energy is repeatedly applied to the blood flow in the blood vessel, either periodically or at irregular time intervals over a period of time, such as during all or a portion of one or more cardiac cycles. A portion of the applied energy is reflected from the blood flow to produce a reflected ultrasonic energy signal. The reflected ultrasonic energy is received for further processing from which blood flow velocity is measured. Electronic circuits are powered off or down between the repeated applications of ultrasonic energy, thereby allowing increased levels of illumination while maintaining or reducing average power consumption.

As described above, one embodiment of the present invention uses strobed ultrasonic energy, which advantageously reduces its average power consumption because portions of the present invention are powered off between strobing instances. This advantage, or a portion thereof, may be traded for improved signal-to-noise ratio (SNR), which is also a desirable characteristic for accurate measurement of blood flow velocity. For example, transducer 160 is capable of providing higher level illumination of blood vessel 105 than in a conventional system, because strobed ultrasonic energy is used, i.e. the higher level illumination is limited to a shorter duration. Since blood vessel 105 is illuminated at a higher level, more reflected energy is available for detection, thereby improving the SNR.

Similar signal processing improvements are also available, for example, by using higher supply currents for shorter durations in those other blocks that are capable of being powered down during the idle period, such as receiver 190, mixer 205, and first and second low pass filters 245 and 265. These signal processing improvements obtained from higher current levels for shorter durations include better noise performance and higher bandwidth. These improvements provided by the present invention are particularly advantageous for the receiver 190 and mixer 205 blocks, which require bandwidths capable of accommodating a Doppler-shifted signal centered around the 5–20 MHz carrier frequency. Thus, the strobed ultrasonic blood flow velocity measurements of the present invention offer considerable advantages in addition to reduced average power consumption.

Trading off the average power savings of the strobed CW Doppler system of present invention for higher power during the active period is further illustrated by way Example 1, comparing the present invention to a conventional CW Doppler system.

| Conventional CW Doppler | Strobed CW Doppler |
|---|---|
| $I_{avg}$ = 2mA | $I_{avg}$ = 2mA |
| | $t_{strobe}$ = 20ms (50 Hz strobing) |
| | $t_{on}$ = 2ms |
| | $t_{off}$ = 18ms |
| | $I_{idle}$ = 500 $\mu$A during $t_{off}$ |
| | $I_{active}$ = 15.5 mA during $t_{on}$ |

Example 1 illustrates, for a 50 Hz strobing frequency and $(t_{on}/t_{strobe})$=10%, the strobed current can be as high as 15.5 mA for an idle current of 500 $\mu$A. Thus, in this example, the current can be elevated by a factor of 7.75 in the strobed CW Doppler system without increasing the average power consumption over a conventional CW Doppler system.

Figure 10:
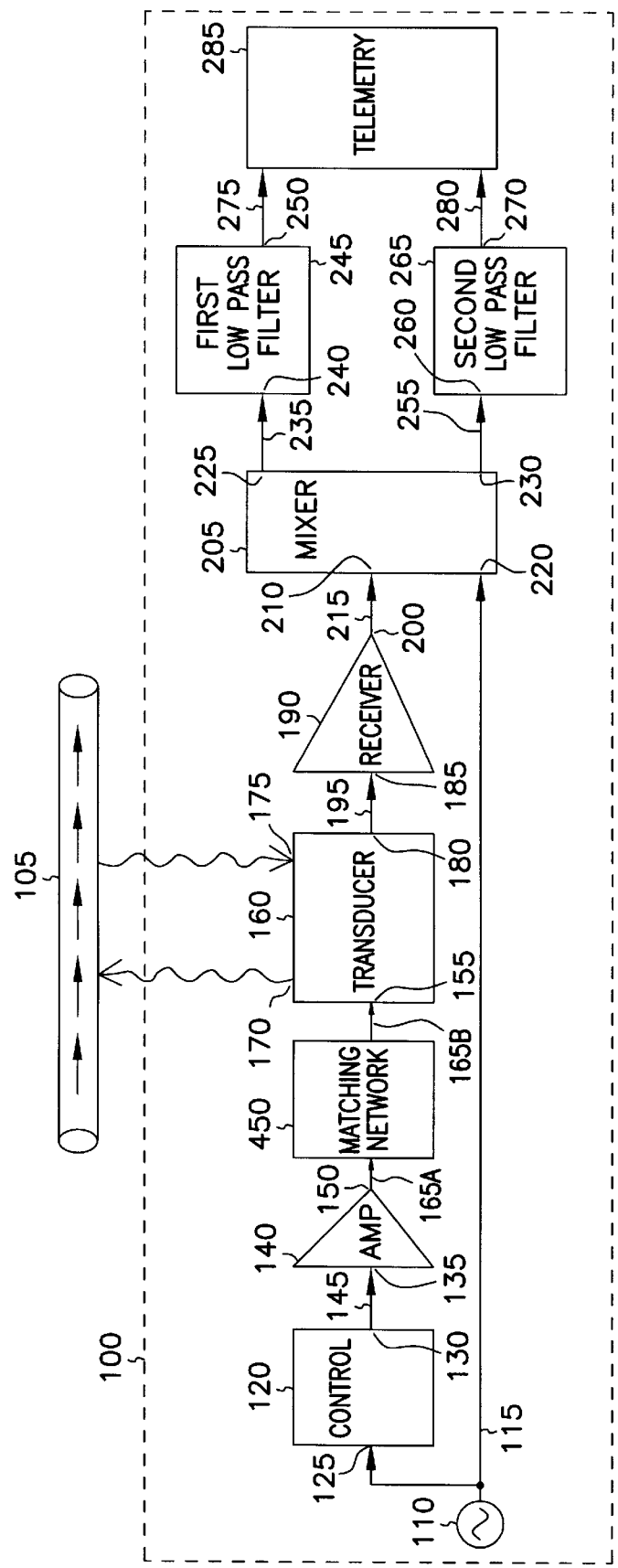
FIG. 10 is a block diagram illustrating an embodiment of the present invention including an impedance matching network.

FIG. 10 is a block diagram illustrating another embodiment of the present invention in which an impedance matching network 450 has been interposed between amplifier output 150 and transducer electrical input 155. Network 450 includes passive impedance matching components to maximize power transfer between amplifier 140 and transducer 160 at the carrier frequency, where amplifier 140 typically presents an impedance that is unmatched to that of transducer 160.

The impedance matching network results in more efficient power transfer at the output of network 450 at node 165B for the strobed CW Doppler system of the present invention over a conventional CW Doppler system, as illustrated in Example 2.

| Conventional CW Doppler | Strobed CW Doppler |
|---|---|
| $Z_{out}$ = 2000$\Omega$ at carrier frequency | $Z_{out}$ =400$\Omega$ at carrier frequency |
| $Z_{tran}$ = 20$\Omega$ at carrier frequency | $Z_{tran}$ = 20$\Omega$ at carrier frequency |
| $Z_{network}$ = 100 to 1 matching | $Z_{network}$ = 20 to 1 matching |
| $I_{amp}$ = 1mA peak | $I_{amp}$ = 5mA peak during active period |
| $V_{amp}$ = 4$V_{p-p}$ continuous | $V_{amp}$ = 4$V_{p-p}$ during active period |
| $P_{amp}$ = 1mW | $P_{amp}$ = 10mW |
| $P_{transducer}$ = 1mW | $P_{transducer}$ = 10mW |
| $V_{transducer}$ = 0.25$V_{p-p}$ | $V_{transducer}$ = 0.89$V_{p-p}$ |

In Example 2: $Z_{out}$ is the output impedance of amplifier 140 at amplifier output 150 at the ultrasonic carrier frequency; $Z_{tran}$ is the impedance of transducer 160 at the carrier frequency; $Z_{network}$ is the impedance matching ratio of network 450; $I_{amp}$ is the peak output current of amplifier 140; $V_{amp}$ is the peak-to-peak output voltage of amplifier 140; $P_{amp}$ is the power output of amplifier 140; $P_{transducer}$ is the power input of transducer 160; and, $V_{transducer}$ is the peak-to-peak input voltage of transducer 160.

In Example 2, the conventional CW Doppler system is operated continuously, and the strobed CW Doppler system is operated at a 10% duty cycle ($t_{on}/t_{strobe}$) with the negligible current during the idle period. As seen in Example 2, amplifier 140 and network 450 of the strobed Doppler system of FIG. 10 allow higher power output from amplifier 140, and a higher input voltage of transducer 160. This produces a higher level illumination, resulting in more reflected ultrasonic energy, and thereby improving the SNR.

FIGS. 1–10 illustrate various embodiments of the present invention in which the basebanded I and Q Doppler signals are telemetered to other circuits for further processing to determine the blood flow velocity estimate. In one embodiment, for example, the basebanded I and Q Doppler signals are telemetered from an implanted portion of the blood flow meter 100 to accompanying external circuits for further processing. However, signal processing of the basebanded I and Q Doppler signals can also be carried out within the implanted blood flow meter 100.

Figure 11:
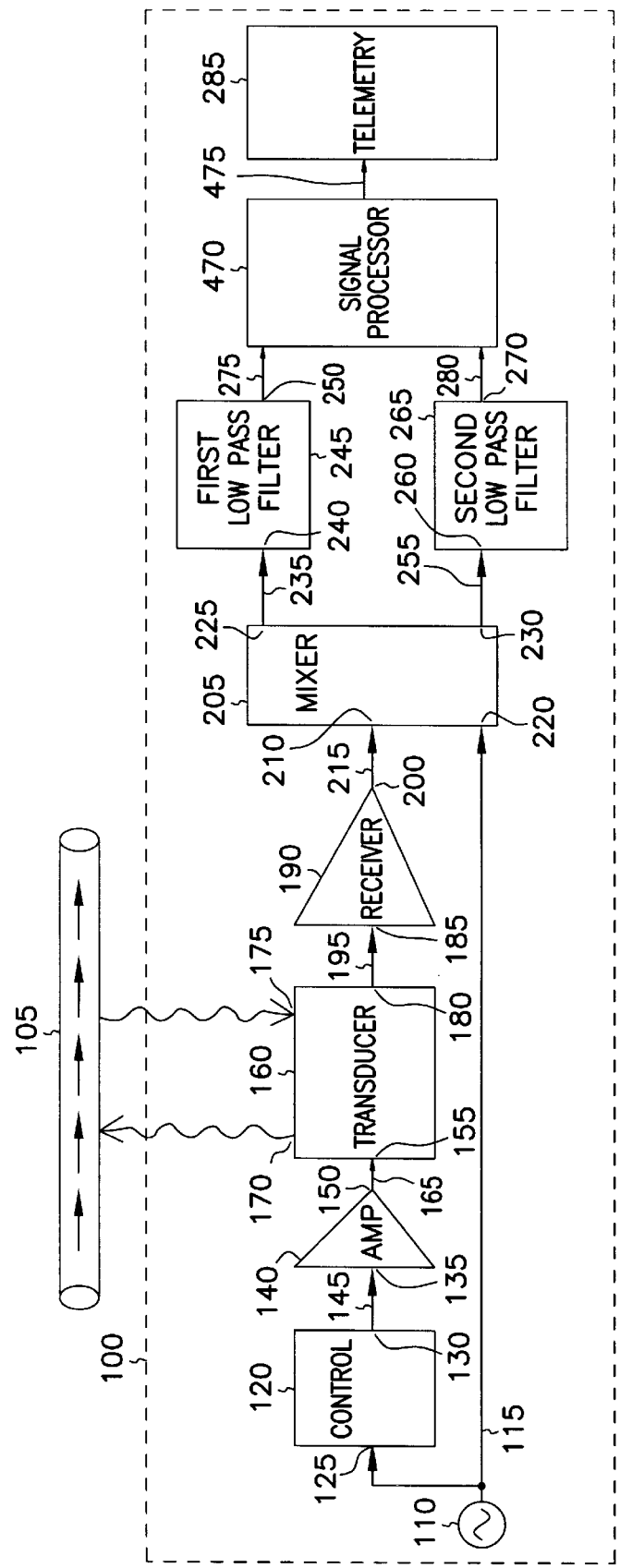
FIG. 11 is a block diagram illustrating an embodiment of the present invention including a signal processor.

FIG. 11 is a block diagram illustrating an embodiment of the present invention in which a signal processor 470 is contained within the implanted blood flow meter 100. In FIG. 11, signal processor 470 receives the basebanded I and Q Doppler signals at respective nodes 275 and 280, and produces a blood flow output signal or velocity output signal representing the estimated blood flow velocity. The velocity output signal is electrically coupled through node 475 to telemetry 285, where it is transmitted from the implanted blood flow meter 100 to an external receiver.

Figure 12:
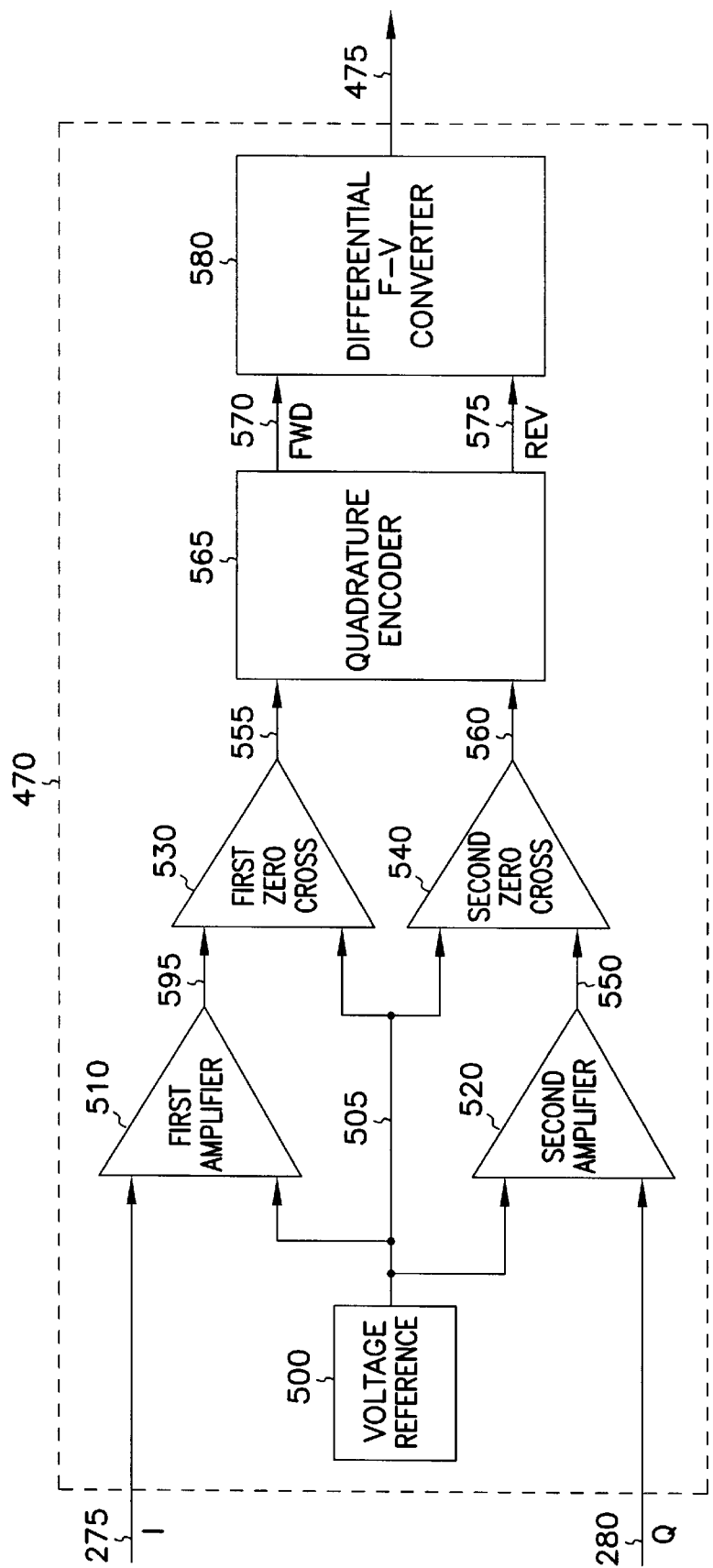
FIG. 12 is a block diagram illustrating one embodiment of the signal processor of FIG. 11 in more detail.

FIG. 12 is a block diagram illustrating one embodiment of signal processor 470 that is particularly useful in applications having a single-ended power supply, such as a battery in the implantable blood flow meter 100 of the present invention. In FIG. 12, signal processor 470 contains a voltage reference 500, which provides a stable output bias voltage at node 505 to a first input of each of first and second amplifiers 510 and 520 and first and second zero cross detectors 530 and 540. First and second amplifiers 510 and 520 provide gain, or provide both gain and level-shifting. First and second amplifiers may also be used to provide bandpass filtering. A second input of first amplifier 510 receives the basebanded I Doppler signal at node 275. A second input of second amplifier 520 receives the basebanded Q Doppler signal at node 280.

First amplifier 510 provides a buffered basebanded I Doppler signal at node 545 to a second input of first zero cross detector 530. Second amplifier 520 provides a buffered basebanded Q Doppler signal at node 550 to a second input of second zero cross detector 540. First and second zero cross detectors 530 and 540 provide first and second zero cross outputs at respective nodes 555 and 560. The first and second zero cross outputs at respective nodes 555 and 560 each change logic state in response to the voltage of respective buffered I and Q Doppler signals passing through the bias voltage at node 505. Each of the resulting pulsatile voltages waveforms at the first and second zero cross outputs is approximately 90 degrees out of phase with the other, and is at the basebanded Doppler frequency.

Quadrature encoder 565 receives the first and second zero cross outputs at respective nodes 555 and 560. The 90 degree phase difference between the voltage waveforms at nodes 555 and 560 make it possible to determine their phase relationship at each logic voltage transition of these voltage waveforms at nodes 555 and 560. Quadrature encoder 565 contains logic circuitry for determining the phase relationship between the first and second zero cross outputs at nodes 555 and 560, and does so at each voltage transition at each of nodes 555 and 560. In response to each such determination, quadrature encoder 565 provides a fixed-duration voltage pulse to only one of forward node 570 or reverse node 575.

Differential frequency-to-voltage converter 580 receives voltage pulses at each of the respective forward and reverse nodes 570 and 575, and provides a resulting blood flow output signal such as the analog velocity output signal at node 475. In one embodiment, converter 580 provides charge integration of the fixed-duration voltage pulses at each of the respective forward and reverse nodes 570 and 575, and provides the resulting blood flow output signal in response thereto. The charge of the voltage pulses at the forward node 570 incrementally increases the velocity output signal at node 475, and the charge of the voltage pulses at the reverse node 575 incrementally decreases the velocity output signal at node 475. Converter 580 could also be implemented as an up-down counter providing an output count representative of the velocity output signal. Voltage pulses received at forward node 570 increment the output count, and voltage pulses received at reverse node 575 decrement the output count, or vice versa.

Thus, signal processor 470 is capable of providing, using a single-ended power supply, an analog velocity output signal at node 475 containing both magnitude and directional information of blood flow velocity. The analog velocity output signal at node 475 can be repeatedly sampled to provide a sequence of blood flow estimates forming a blood flow waveform indicative of blood flow. The analog velocity output signal at node 475 or the samples derived therefrom can be further processed and transmitted from the implanted blood flow meter 100.

FIGS. 1–12 illustrate various bidirectional embodiments of the present invention that are capable of determining the magnitude and direction of blood flow velocity. If direction information is not needed, a unidirectional embodiment of the present invention could be used. In a unidirectional embodiment of the present invention, one of the I or Q channels is omitted. In mixer 205, a quadrature phase splitter 300 is omitted and only one of first and second multipliers 305 and 310 is needed. In signal processor 470, quadrature encoder 565 is replaced by a monostable oscillator (one-shot) providing a fixed-duration pulse, and differential frequency-to-voltage converter 580 is replaced by a single-ended frequency-to-voltage converter.

The present invention has been described above with respect to a particular embodiment of strobed ultrasonic Doppler blood flow meter, i.e. a strobed continuous wave (CW) ultrasonic Doppler blood flow meter, referred to as a strobed CW Doppler blood flow meter. However, it is understood that the present invention is also broadly applicable to any embodiment of a strobed ultrasonic Doppler blood flow meter and its method of use.

For example, the invention encompasses the use of a strobed ultrasonic pulsed Doppler blood flow meter, referred to as a strobed pulsed Doppler blood flow meter. The strobed pulsed Doppler embodiment also periodically illuminates a blood vessel by a transducer, but each illumination comprises bursts of pulsatile (or pulse train) ultrasonic-frequency energy. Each burst of ultrasonic-frequency energy from a particular illumination is reflected, or backscattered, from the blood flow and typically subsequently detected at the same transducer. Samples of the resulting electrical signal, each corresponding to a burst of pulsatile ultrasonic-frequency energy, are used to estimate mean frequency. A resulting blood flow velocity estimate is produced from the aggregation of mean frequency estimations within a particular strobing.

Figure 13:
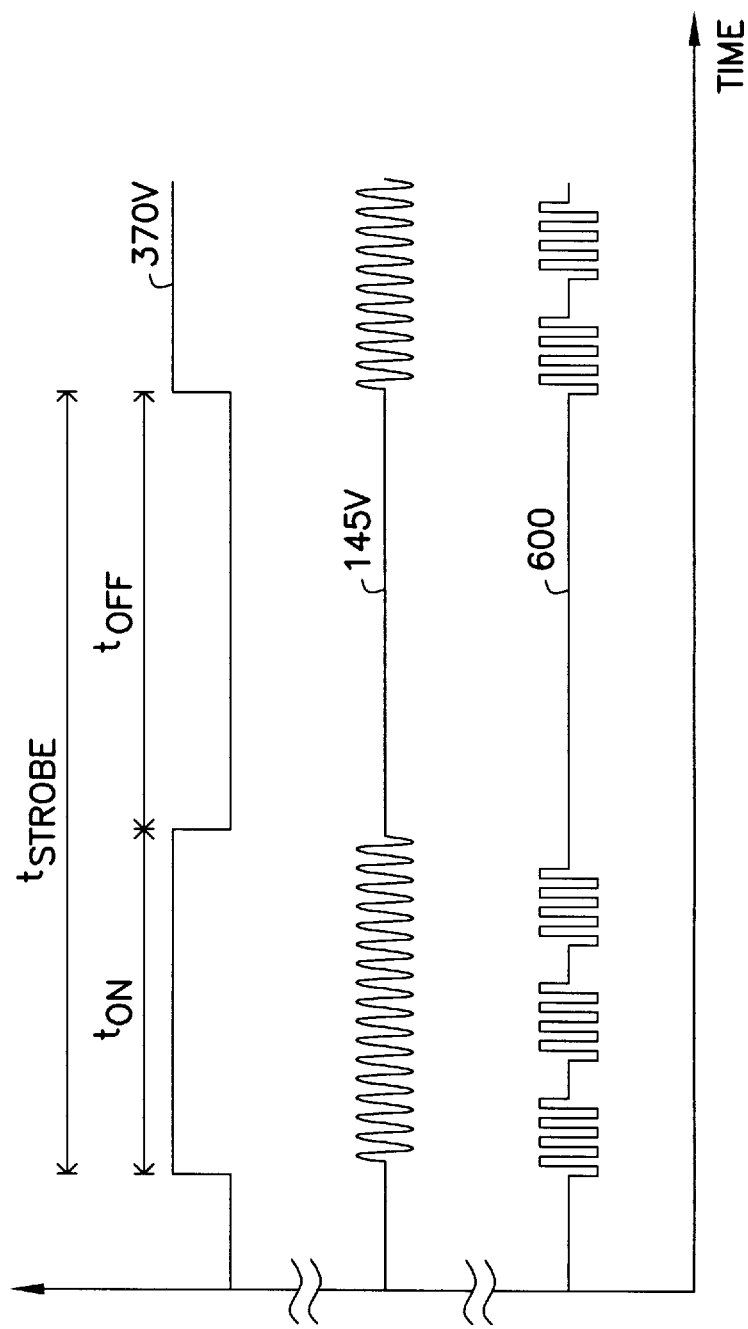
FIG. 13 is a graph generally comparing the strobed continuous wave and pulse Doppler ultrasonic frequency waveforms.

FIG. 13 illustrates generally a comparison of the strobed ultrasonic frequency signal waveforms used in each of the strobed CW and strobed pulsed Doppler embodiments. In FIG. 13, the strobing control signal 370V illustrates generally the active and idle periods in relation to the strobing period. The CW embodiment provides an ultrasonic frequency signal 145V continuously over the entire active period or at least some portion thereof. The strobed pulsed Doppler embodiment provides a pulsed ultrasonic frequency signal 600 that typically contains more than one burst of pulsatile ultrasonic-frequency energy over the active period or at least some portion thereof.

In fact, as illustrated in FIG. 13, the type of ultrasonic energy signal used is not essential to the invention. Thus, both of the above-described ultrasonic blood flow meters have characteristics that include: repeatedly illuminating the blood vessel with ultrasonic energy during a cardiac cycle; repeatedly receiving during the cardiac cycle an ultrasonic energy signal, which contains Doppler-shifted frequencies corresponding to a blood flow velocity estimate, reflected from the blood flow; and, processing the received ultrasonic energy signal to obtain the blood flow velocity estimate from the Doppler-shifted frequencies contained therein.

In both species of strobed ultrasonic blood flow meters, the ultrasonic energy is strobed repeatedly throughout the cardiac cycle or other period of interest, with a strobing frequency which is substantially lower than the ultrasonic energy frequency. In one embodiment of the present invention, each strobing instance corresponds to a resulting blood flow velocity estimate.

The above-described embodiments describe a blood flow meter that estimates blood flow velocity by strobed Doppler measurements of backscattered ultrasonic energy. However, the strobed blood flow meter according to the present invention also includes other techniques of estimating blood flow velocity, including, but not limited to: transit time measurements, electromagnetic flow measurements, thermal dilution measurements, and laser Doppler measurements, each of which is described further below.

Figure 14:
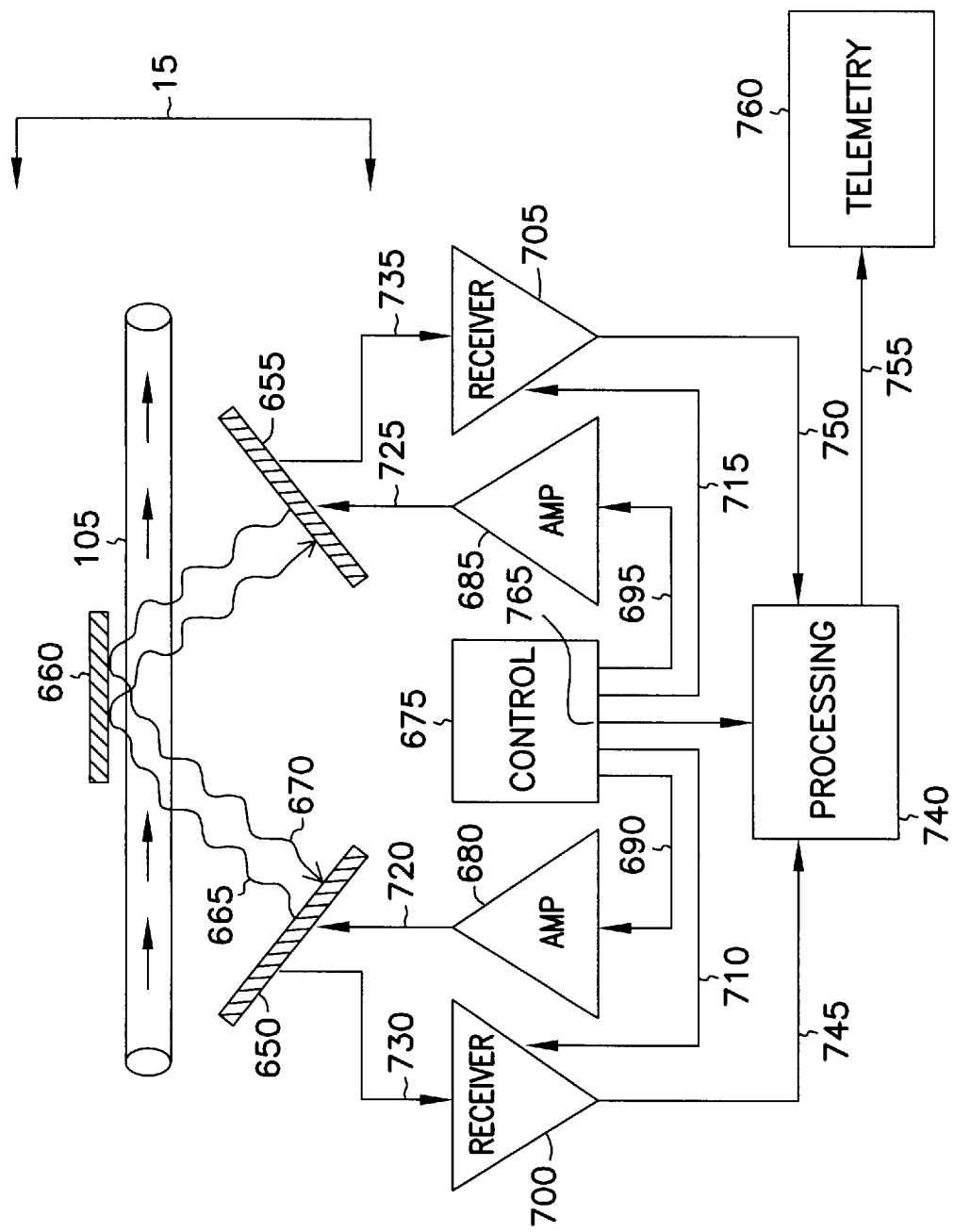
FIG. 14 is a block diagram illustrating one embodiment of the present invention using transit time techniques of blood flow velocity estimation.

FIG. 14 is a generalized schematic illustration of one embodiment of a transit time measurement of blood flow velocity that is encompassed by the present invention. First and second transducers 650 and 655, respectively, are configured for ultrasonic communication therebetween via an acoustic reflector 660. A first ultrasonic impulse 665 is launched from first transducer 650, reflected from reflector 660, and received at second transducer 655. A second ultrasonic impulse 670 is launched from second transducer 655, reflected from reflector 660, and received at first transducer 650.

FIG. 14 illustrates the case where first impulse 665 has a directional component in the same direction as the blood flow in blood vessel 105, and second impulse 670 has a directional component opposite the direction of blood flow in blood vessel 105. As a result, a travel time of second impulse 670 from second transducer 655 to first transducer 650 is longer than a travel time of first impulse 665 from first transducer 650 to second transducer 655. Blood flow velocity is calculated from the difference in transit times of the first and second impulses 665 and 670 respectively.

In this embodiment, the invention includes a control circuit 675 for providing a strobed ultrasonic frequency signal to each of respective first and second amplifiers 680 and 685 through respective nodes 690 and 695. Control circuit 675 optionally provides power control signals to respective first and second receivers 700 and 705 through respective nodes 710 and 715. First and second amplifiers 680 and 685, respectively, provide an amplified strobed ultrasonic frequency signal at respective nodes 720 and 725 to respective first and second transducers 650 and 655, which provide the first and second impulses 665 and 670 in response thereto.

First and second transducers 650 and 655 also receive respective second and first impulses 670 and 665, as described above, and provide resulting electrical signals to respective first and second receivers 700 and 705 through respective nodes 730 and 735. First and second receivers 700 and 705, respectively, provide buffered electrical signals to processing circuit 740 through respective nodes 745 and 750. Processing circuit 740 calculates blood flow velocity from the difference in transit times of the first and second impulses 665 and 670 respectively, and provides through node 755 a signal containing blood flow velocity information to telemetry device 760 for transmission to a remote telemetry device. Control circuit 675 optionally provides a power control signal to processing circuit 740 through node 765 for reducing or removing power from processing circuit 740 between transit time estimates of blood flow velocity. As described above, control circuit 675 may also optionally provide a power control signal to telemetry device 760 to reduce or remove power from telemetry device 760 when it is not transmitting a transit time estimate of blood flow velocity.

Figure 15:
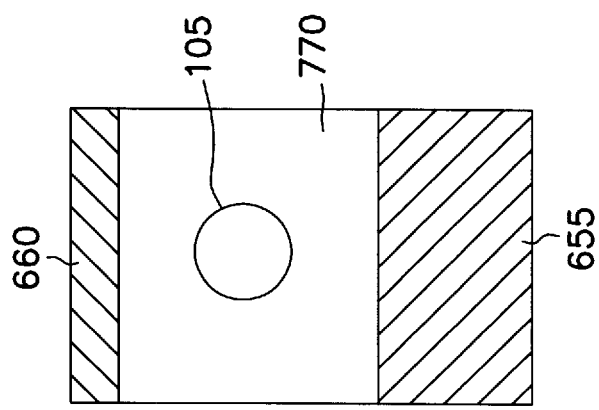
FIG. 15 is an end view of the embodiment illustrated in FIG. 14.

FIG. 15 illustrates an end view of the configuration of FIG. 14. In FIG. 15, first and second transducers 650 and 655, respectively, and reflector 660 are arranged such that first and second impulses 665 and 670, respectively, each provide an insonification area 770 that includes the entire area of blood vessel 105, such that an average estimate of blood flow over the area of blood vessel 105 is provided. The transit time estimate of blood flow velocity may also be improved by averaging multiple transit time measurements to provide a single estimate of blood flow velocity. In such an embodiment, control circuit 675 reduces or removes power from other circuits between each series of transit time measurements used to provide a blood flow velocity estimate. A sequence of blood flow estimates forms a waveform representative of blood flow over a period of time.

The present invention also includes the use of electromagnetic flow techniques to estimate blood flow velocity. In one embodiment of this technique, first and second electrodes are disposed across an interposed blood vessel such that the blood flow is in a direction that is substantially orthogonal to a vector between the first and second electrodes. A permanent magnet or electromagnet is used to create a magnetic field through the blood vessel in a direction that is substantially orthogonal to both the direction of blood flow and the vector between the first and second electrodes. As a result, ionized particles within the blood flow are deflected toward one of the first and second electrodes, resulting in a voltage difference therebetween that is proportional to the blood flow velocity. The invention uses the above-described strobing technique to reduce or remove power between blood flow estimates to circuits within the blood flow meter, such as to the electromagnet, if any, or to sensing and processing circuits that detect the voltage difference between the first and second electrodes, or to telemetry circuits that transmit electromagnetic flow estimates of blood flow velocity to a remote telemetry device.

The present invention also includes the use of thermal dilution techniques to estimate blood flow. In one embodiment of this technique, a heater is used to pulsedly heat the blood, and the heated blood pulse is detected by a temperature sensor located at a known distance from the point of heating in the direction of the blood flow. Volumetric blood flow is calculated from the time between the heating of the blood pulse and the detection of the blood pulse. Several heated blood pulses are typically introduced and detected to produce a more accurate blood flow estimate.

In another embodiment of this technique, a single thermistor is used for both heating and detection. A heated thermistor is introduced into the blood vessel such that it is in thermal contact with the blood flow, and cooling of the thermistor is effected by the blood flow. Blood flow at a higher velocity cools the thermistor at a higher rate than blood flow at a lower velocity. The energy delivered to the thermistor to maintain the thermistor at a constant temperature is proportional to blood flow velocity. Alternatively, the thermistor can be heated to a known temperature, and the time required to cool the thermistor to a second, lower temperature will be inversely proportional to blood flow.

According to the present invention, measuring circuits in the above-described thermal dilution embodiments are automatically activated only during estimation of blood flow, and are powered down or off between estimates of blood flow. A resulting volumetric blood flow vs. time waveform constructed from the sequence of blood flow estimates is thereby obtained at a reduced power consumption by application of the strobing technique of the present invention.

The present invention also includes the use of laser Doppler techniques to estimate blood flow. The blood flow is illuminated with a coherent monochromatic light source signal. A resulting backscattered Doppler-shifted light signal is received at an optical detector, and demodulated such as by mixing with the monochromatic light source signal. Blood flow velocity is estimated from a resulting basebanded Doppler-shifted frequency of the received light signal. According to the present invention, measuring circuits, optionally including the monochromatic light source, are automatically activated only during estimation of the blood flow velocity. These measuring circuits are deactivated, i.e. powered down or off between estimates of blood flow velocity. A resulting velocity vs. time waveform constructed from the sequence of blood flow velocity is thereby obtained at a reduced power consumption by application of the strobing technique of the present invention.

Thus, the present invention provides an strobed blood flow meter, such as an implantable strobed ultrasonic Doppler blood flow meter, having reduced average power consumption, which is advantageous for reducing battery size, improving signal-to-noise ratio, and extending battery life.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An apparatus for repeatedly estimating blood flow in a vessel over a period of time, the apparatus comprising:
   one or more transducers;
   a source of electrical excitation signal that is applied to at least one of the one or more transducers for an active period of a control signal sufficient to obtain a blood flow estimate and is removed from the at least one of the one or more transducers for an idle period of the control signal until a subsequent blood flow estimate is to be obtained.

2. The apparatus of claim 1, further comprising a source of one or more power control signals applied to the source of the excitation signal such that the source of the excitation signal is powered down or off for at least a portion of the idle period.

3. The apparatus of claim 1, further comprising an implantable housing containing the source of the electrical excitation signal.

4. The apparatus of claim 3, further comprising a telemetry device, contained within the housing, for transmitting from the implantable apparatus one or more signals containing information indicative of the blood flow estimate.

5. The apparatus of claim 4, further comprising a source of one or more power control signals applied to the telemetry device such that the telemetry device is powered down or off when not transmitting signals from the implantable apparatus.

6. The apparatus of claim 1, wherein the period of time is a cardiac cycle in a living organism.

7. An apparatus for obtaining a Doppler-shifted ultrasonic energy signal for repeatedly estimating blood flow, the apparatus comprising:
   a control circuit that provides an electrical ultrasonic-frequency signal containing ultrasonic-frequency components during an active period of a control signal that is of sufficient duration to obtain a blood flow estimate, and contains substantially no ulstrasonic-frequency components during an idle period of the control signal between the active period and a subsequent active period;
   an amplifier having an amplifier input, which is electrically coupled to the control circuit for receiving the strobed ultrasonic-frequency signal, and an amplifier output providing an electrical strobed amplified ultrasonic-frequency signal in response thereto;
   an ultrasound transducer having a transducer electrical input, which is electrically coupled to the amplifier output for receiving the amplified ultrasonic-frequency signal, and having a transducer ultrasound output, for providing strobed ultrasonic energy to the blood vessel in response to the amplified ultrasonic-frequency signal, and having a transducer ultrasound input, for receiving a reflected Doppler-shifted ultrasonic energy signal from the blood vessel, and having a transducer electrical output, for providing an electrical received Doppler-shifted signal in response thereto; and
   a receiver having a receiver input electrically coupled to the transducer electrical output for receiving the received Doppler-shifted signal and having a receiver output for providing a buffered Doppler-shifted signal in response thereto.

8. The apparatus of claim 7, wherein the ultrasound transducer comprises:
   a transmit transducer, which is electrically coupled to the amplifier output for receiving the amplified ultrasonic-frequency signal and providing ultrasonic energy to the blood vessel in response thereto; and
   a receive transducer, for receiving the reflected Doppler-shifted ultrasonic energy signal from the blood vessel and providing the received Doppler-shifted signal in response thereto.

9. The apparatus of claim 7, further comprising a mixer having a mixer input electrically coupled to the receiver output for receiving the buffered Doppler-shifted signal, and having an in-phase mixer output providing in response thereto an in-phase signal having difference and sum frequency components that are approximately equal to the respective difference and sum of the frequencies of the ultrasonic-frequency signal and the buffered Doppler-shifted signal.

10. The apparatus of claim 9, wherein the mixer includes a phase-shifted mixer output providing in response to the buffered Doppler-shifted signal a phase-shifted signal having difference and sum frequency components that are approximately equal to the respective difference and sum of the frequencies of the ultrasonic-frequency signal and the buffered Doppler-shifted signal.

11. The apparatus of claim 10, further comprising a second low pass filter having a second low pass filter input electrically coupled to the phase-shifted mixer output for receiving the phase-shifted signal, and having a second low pass filter output providing a basebanded phase-shifted Doppler signal in response thereto.

12. The apparatus of claim 11, further comprising a telemetry circuit coupled to the second low pass filter output for receiving, and transmitting therefrom, the basebanded phase-shifted Doppler signal.

13. The apparatus of claim 12, further comprising a remote telemetry device that is wirelessly coupled to the telemetry circuit for receiving the basebanded phase-shifted Doppler signal that is transmitted therefrom.

14. The apparatus of claim 11, further comprising a first low pass filter having a first low pass filter input electrically coupled to the in-phase mixer output for receiving the in-phase signal, and having a first low pass filter output providing a basebanded in-phase Doppler signal in response thereto.

15. The apparatus of claim 14, further comprising a signal processor for providing a blood flow velocity signal in response to the basebanded in-phase and phase-shifted Doppler signals.

16. The apparatus of claim 14, wherein the signal processor comprises:
   a first zero crossing detector, electrically coupled for receiving the basebanded in-phase Doppler signal, and providing a first zero cross output in response thereto;
   a second zero crossing detector, electrically coupled for receiving the basebanded phase-shifted Doppler signal, and providing a second zero cross output in response thereto;
   a quadrature decoder, electrically coupled for receiving each of the first and second zero cross outputs, and providing in response to each voltage transition thereof, a fixed duration voltage pulse at one of a forward and reverse output nodes; and a differential frequency-to-voltage converter, electrically coupled for receiving the fixed duration voltage pulse at each of the forward and reverse output nodes, and providing in differential response thereto, a velocity output signal.

17. The apparatus of claim 9, further comprising a first low pass filter having a first low pass filter input electrically coupled to the in-phase mixer output for receiving the in-phase signal, and having a first low pass filter output providing a basebanded in-phase Doppler signal in response thereto.

18. The apparatus of claim 17, fuirther comprising a telemetry circuit coupled to the first low pass filter output for receiving, and transmitting therefrom, the basebanded in-phase Doppler signal.

19. The apparatus of claim 18, further comprising a remote telemetry device that is wirelessly coupled to the telemetry circuit for receiving the basebanded in-phase Doppler signal that is transmitted therefrom.

20. The apparatus of claim 7, further comprising an impedance matching network series-connected between the amplifier and the transducer for improving power transfer therebetween.

* * * * *

UNITED STATES PATENT AND TRADEMARK OFFICE
CERTIFICATE OF CORRECTION

PATENT NO. : 5,865,749

DATED : February 2, 1999

INVENTOR(S) : Gregory P. Doten et al.

It is certified that error appears in the above-identified patent and that said Letters Patent is hereby corrected as shown below:

On the title page,
At [57] Abstract: please delete "to an remote" and insert --to a remote--.

At Col. 1, line 3, please add --Notice of Federally Sponsored Research - Portions of this invention were developed under Contract No. 1 R43 HL52399-01, awarded by the National Institutes of Health. Therefore, the U.S. Government may have a paid-up license in portions of this invention and the right, in limited circumstances, to require the patent owner to license others on reasonable terms as provided for by the terms of the contract.--.

At Col. 9, line 39, please add the heading --EXAMPLE 1--.

At Col. 10, line 1, please add the heading --EXAMPLE 2--.

At Col. 14, line 66, please omit "provides an strobed" and insert --provides a strobed--

Signed and Sealed this

Twenty-ninth Day of June, 1999

Attest:

Q. TODD DICKINSON

Attesting Officer

Acting Commissioner of Patents and Trademarks